US006969835B1

(12) United States Patent
Rushbrooke et al.

(10) Patent No.: US 6,969,835 B1
(45) Date of Patent: Nov. 29, 2005

(54) IMAGING ASSAY ANALYSIS FOR MICROSAMPLES

(75) Inventors: John Gordon Rushbrooke, Newport Beach, CA (US); Claire Elizabeth Hooper, Newport Beach, CA (US)

(73) Assignee: Packard Instrument Company Inc., Meridian, CT (US)

( * ) Notice: Subject to any disclaimer, the term of this patent is extended or adjusted under 35 U.S.C. 154(b) by 0 days.

(21) Appl. No.: 09/979,818

(22) PCT Filed: Apr. 14, 2000

(86) PCT No.: PCT/GB00/01448

§ 371 (c)(1),
(2), (4) Date: Feb. 26, 2002

(87) PCT Pub. No.: WO01/01115

PCT Pub. Date: Jan. 4, 2001

(30) Foreign Application Priority Data

Jun. 29, 1999 (GB) .................................... 9150344

(51) Int. Cl.⁷ ............................................. F21V 9/16
(52) U.S. Cl. .................................. 250/208.1; 356/317

(58) Field of Search ......................... 250/208.1, 458.1, 250/459.1; 356/451, 317; 435/287.2

(56) References Cited

U.S. PATENT DOCUMENTS

| 4,271,123 A | 6/1981 | Curry et al. .................. 422/64 |
| 5,991,030 A * | 11/1999 | Yamamoto et al. ......... 356/451 |
| 6,596,483 B1 * | 7/2003 | Choong et al. ................ 436/6 |

FOREIGN PATENT DOCUMENTS

| EP | 0 902 280 | 3/1999 |
| EP | 0 973 040 | 1/2000 |
| WO | WO 98/01743 | 1/1998 |
| WO | WO 00/06996 | 2/2000 |

* cited by examiner

Primary Examiner—Stephone B. Allen
(74) Attorney, Agent, or Firm—Barnes & Thornburg

(57) ABSTRACT

A system for imaging radiation emitted by assay couples into a photoelectric detector, the system including a fibre optic bundle (100) for conveying light to the detector, wherein a microlens (118), preferably a drum lens, is located at the impact end of the fibre optic bundle to match the field of view of the bundle to a potential area of interest in a sample.

16 Claims, 4 Drawing Sheets

Figure 1:
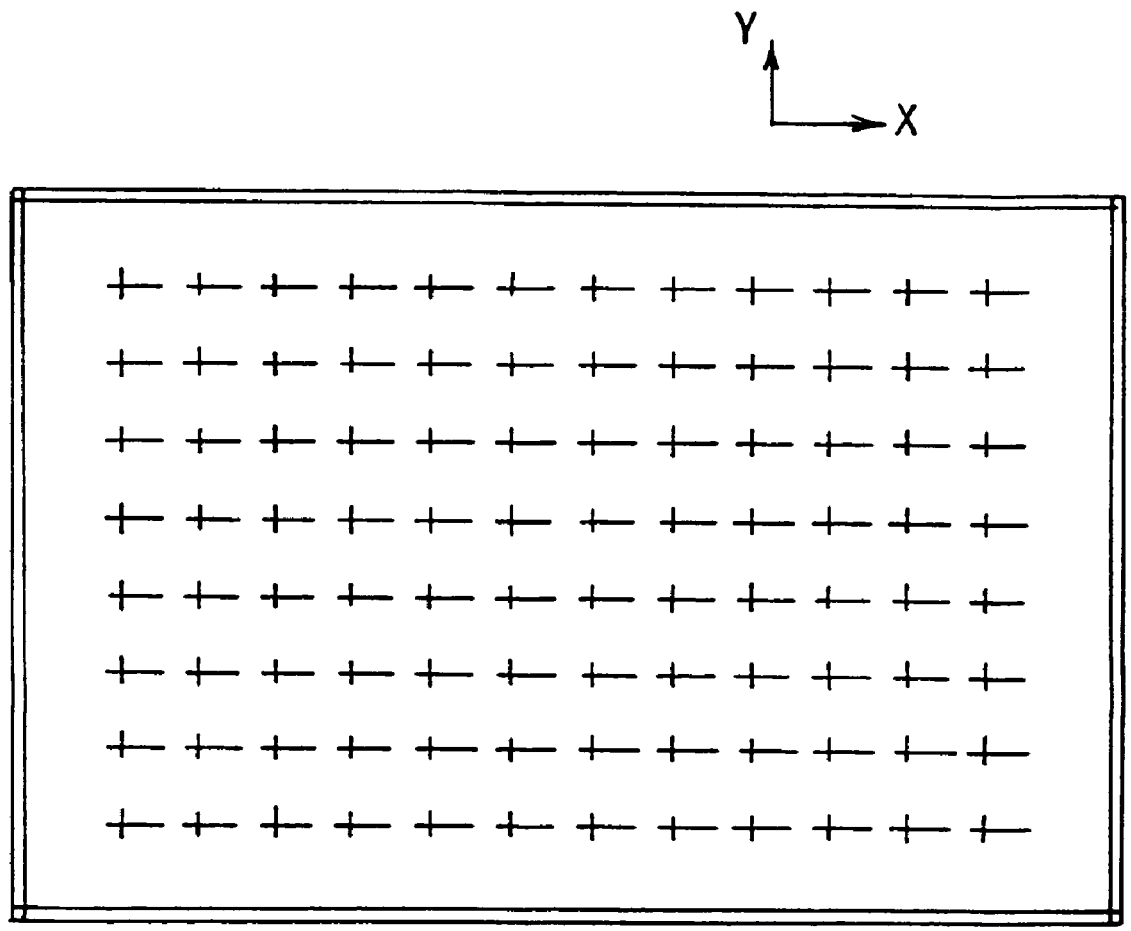

Example of microcapillary channels in an 8 x 12 pattern, similar to the wells in a 96-well microtitre plate High density miniaturised well format presentation having 3456 wells Enlarged view of part of a high density gridded array of, eg, DNA

IMAGING ASSAY ANALYSIS FOR MICROSAMPLES

FIELD OF INVENTION

This invention relates to the measurement of radiation, typically fluorescence emitted by samples and assays in the field of biological, bio-medical and chemical sciences.

BACKGROUND TO THE INVENTION

Such assays are normally prepared and measured in sample plates or formats, including 96-well microtitre plates, petri dishes, gel matrices, membranes, glass slides and capillaries. The trend is towards higher throughput detection of samples and the use of smaller volumes in each of the samples, resulting in so- called miniaturised sample formats.

This requires the corresponding development of detectors capable of handling such miniaturised formats. This is particularly so in the case of high throughput screening (HTS) of biological assays as applied to drug discovery and the screening of drug candidates.

Such miniaturisation is achieved by arraging samples for assay and detection in well plates in which typically there can be 96, 384, 864, 1536 or 3456 wells per plate, and sample volumes can vary from 200 microlitres to as little as 1 microlitre.

Alternative formats for the miniaturisation of assays include capillaries, microchannels or microfluidic structures, including microwells, which can be moulded or etched in substrates such as glass (eg silica or quartz) or plastic. In these alternative formats, the sample volumes can be of the order of nanolitres and picolitres.

In order to achieve high throughput screening it is necessary to interrogate large numbers of such samples simultaneously. In the case of fluorescence based assays, detection or interrogation consists of illuminating each sample with excitation light, and subsequently detecting the emitted fluorescence from each sample separately. Examples of fluorescent based processes include prompt fluorescence and time-resolved fluorescence where there is a time delay between photoactivation of the sample and emission, in the range, for example of ps to ms or more. A further process is fluorescence or luminescence energy transfer. In this process a molecule is activated, for example by excitation light, and transfers energy via eg resonance energy transfer or chemical transfer to a second molecule, which in turn emits light. This process can involve different or multiple secondary molecules, which can emit radiation over a range of wavelengths. Further examples of luminescent processes include phosphorescence, and chemi- and bio-luminescence. Wavelength ranges for all these processes include UV, visible, red and infra-red (approx 250–1200 nm).

In a typical arrangement, a scanning head with 96-channels simultaneously interrogates the 96-sites arranged in the 8×12 pattern of a 96-well microtitre plate. By stepping a higher well-density relative to a 96-channel scanning head, the remaining sites can be read. Eg 2×2 steps will cover 384-samples, 6×6 steps will cover 3456 samples, and so on. This allows the head to address higher density sample presentation formats.

Fluid samples, eg liquids or gels, can be placed in small sample sites, such as micro-capillaries or microchannels, which can be typically 100×100 um in section, and typically 1–100 mm long. The samples can be moved by pumps, or electrophoretically or electro-osmotically. Samples can be solid or a matrix, such as beads, agarose or microparticles, suspended or otherwise contained in a fluid medium, including a gel type format. Other samples can comprises suspensions or monolayers of cells.

Applications include cell biology, hybridisation techniques and immunoassays including binding assays. In such assays, materials can be labelled with a fluorescence marker for the purpose of identification. In a binding assay, a bound molecule can be separated from an unbound molecule, as between a solid and liquid medium. Further applications include electrophoresis or electro-osmosis fluids such as liquids, gels and media including agarose. Such applications can be run in miniaturised formats including micro-capillaries and micro- fluidic structures, where molecules or moities may be separated spatially by properties including molecular weight or charge and may also be labelled with fluorescent or luminescent tags or dyes for the purpose of detection and identification. The techniques described herein can be applied to the detection of biological compounds including proteins and nucleic acids, and in cell biology, processes such as cell signalling or cell binding can also be detected.

Separated molecules can be contained in a fixed matrix, such as a gel or agarose beads, or can be separated in a fluid such that the separated molecules or moities will flow at different rates through a medium and can be detected at a fixed point along the flow path as a series of emission peaks based on their time separation profile. It is important that emission detection methods posses high accuracy and sensitivity for the determination of such peaks, and the rapid and/or continuous and/or simultaneous measurement of samples.

A number of such assay techniques involve time changes in light emission. To measure such changes requires an ability to perform rapid, accurate, sensitive and repetitive readings, that is to perform kinetic measurements. In order to achieve high throughput it is necessary for a system to measure multiple samples simultaneously, requiring high resolution, high sensitivity and high signal detection efficiency.

Mostly the samples/assays are arranged to emit light in the middle range, although the quantities of light per sample can be very low.

A further issue with fluorescence-based assays is the problem of quench which causes a reduction in light emission. This can occur in samples and assays particularly those involving cells, due to chemical effects which interfere with the light signal, or due to coloured substances or particles in the sample or medium, which reduce the light signal. In certain applications, such as inhibition assays, a change or reduction in light signal is the feature of the assay requiring measurement.

FIG. 1(*a*) shows an array of 8×12 micro capillaries in a substrate, in which either a liquid, or molecules or moieties in a fluid, move in the X-direction. This is an example of an array of miniaturised samples such as will be referred to in this application.

FIGS. 1(*b*) and 1(*c*) show further examples of arrays that involve high density or miniaturised sample formats.

Imaging systems for detecting epi-fluorescence are known. Typically, as shown in FIGS. 1(*a*) to (*c*) of the accompanying drawings, an array of 96 fibre optic bundles is arranged to align with the centre of each of a plurality of sample sites on a sample plate—such as an 8×12 matrix 96 well plate, each well typically having a diameter of the order of 1 mm.

OBJECT OF THE INVENTION

It is an object of the present invention to provide a system for imaging radiation emitted by assay samples onto a photosensitive detection, whereby to enable much smaller samples (commonly referred to as micro-samples) to be inspected. Typically micro-samples have one dimension which is less than 500 microns, and can be as small as 50 microns or less.

SUMMARY OF THE INVENTION

According to the present invention, an additional optical imaging device is located at the input end of a fibre optic bundle of an imaging system said bundle being adapted to convey light from the input end thereof to a photosensitive detector, such as a CCD array, the properties of the additional device being such as substantially to match the size of the input end of the bundle to the size and NA of a micro-sample by appropriate choices of numerical aperture for the additional device, so as to reduce the field of view of the bundle to substantially the area of the region of interest of a micro-sample to allow the bundle to view just one micro-sample, and secondly to increase the light collecting properties of the bundle in relation to small light emitting areas.

Where the bundle has a diameter of typically 1.4 mm, and an NA typically of 0.22 the optical device requires to have a NA of approximately 0.7 if the sample has a diameter of the order of 130 microns.

A preferred said additional optical device comprises a micro lens and is preferably a ball lens, more preferably a so-called drum lens.

Preferably an apertured plate is located between the samples and the input end of the bundle, each aperture being aligned with one of the micro-samples, and the additional device is located between the aperture and the bundle which is to receive light from that aperture.

The advantage gained by the use of an apertured plate is that background illumination passing to the bundle is reduced.

When the samples are generally circular, the apertures are also preferably circular. Where the samples are elongate (as can be the case where the samples comprise micro capilliaries), the aperture may be square or rectangular and dimensioned to allow for tolerance in the size and lateral position of the micro-samples as determined by the lateral position of a microcapillary in a sample array.

Utilising an additional optical device having the above properties, in combination with a background reducing aperture, when the sample and bundle have the above dimensions and NA, will increase the light collecting properties of the bundle per unit volume of the sample, by a factor in the range 10 to 20.

Figure 1B:
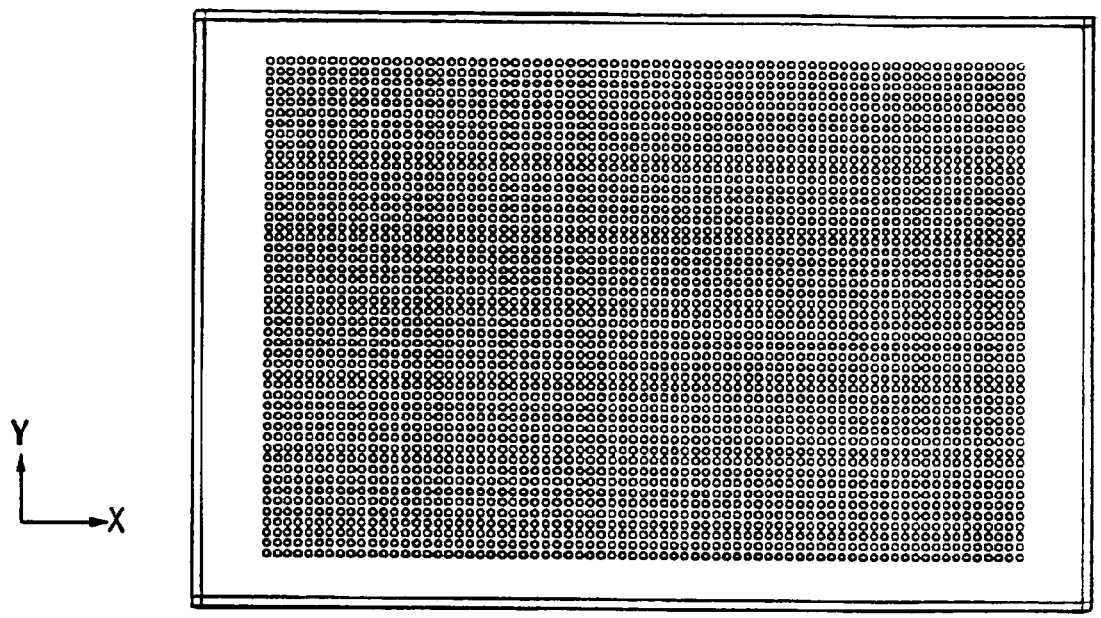
Figure 1C:
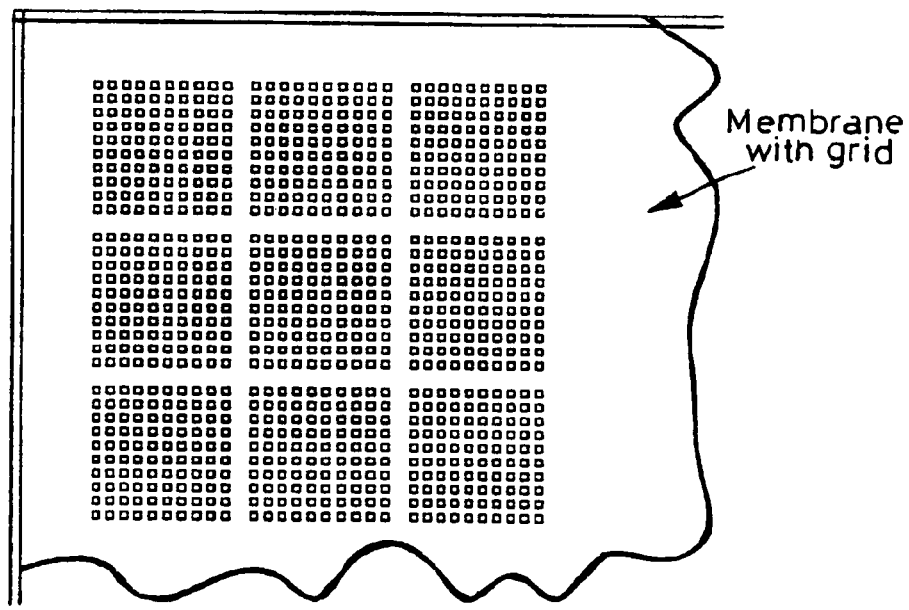

Examples of microcapillary arrays are shown in FIGS. 1(a) to (c) of the accompanying drawings.

The main source of background illumination (as opposed to sample fluorescence) arises from light emitted by the walls and base of a microcapillary or microwell.

In the case of a microcapillary, the background will tend to remain constant, whereas the fluorescence due to the presence of cells or cell clusters in a fluid flowing through the channel of the microcapillary, will tend to vary. Therefore errors in measuring background levels will tend to be Poissoin errors, and it can be expected that these will dominate any systematic errors.

In a preferred arrangement the sample is systematically scanned for example by moving the plate containing the micro capilliaries or microwells relative to the array of fibre optic bundles and associated microlenses.

Preferably each microlens has an appropriate anti-reflective coating selected to take account of the range of excitation and emission wavelengths associated with the assay.

Preferably each microlens is constructed from low fluorescence material and one having an appropriate refractive index.

High quality sapphire is to be preferred for the microlens material.

The invention will now be described, by way of example, with reference to:

FIGS. 1a–1c of the accompanying drawings, as already referred to

Figure 2:
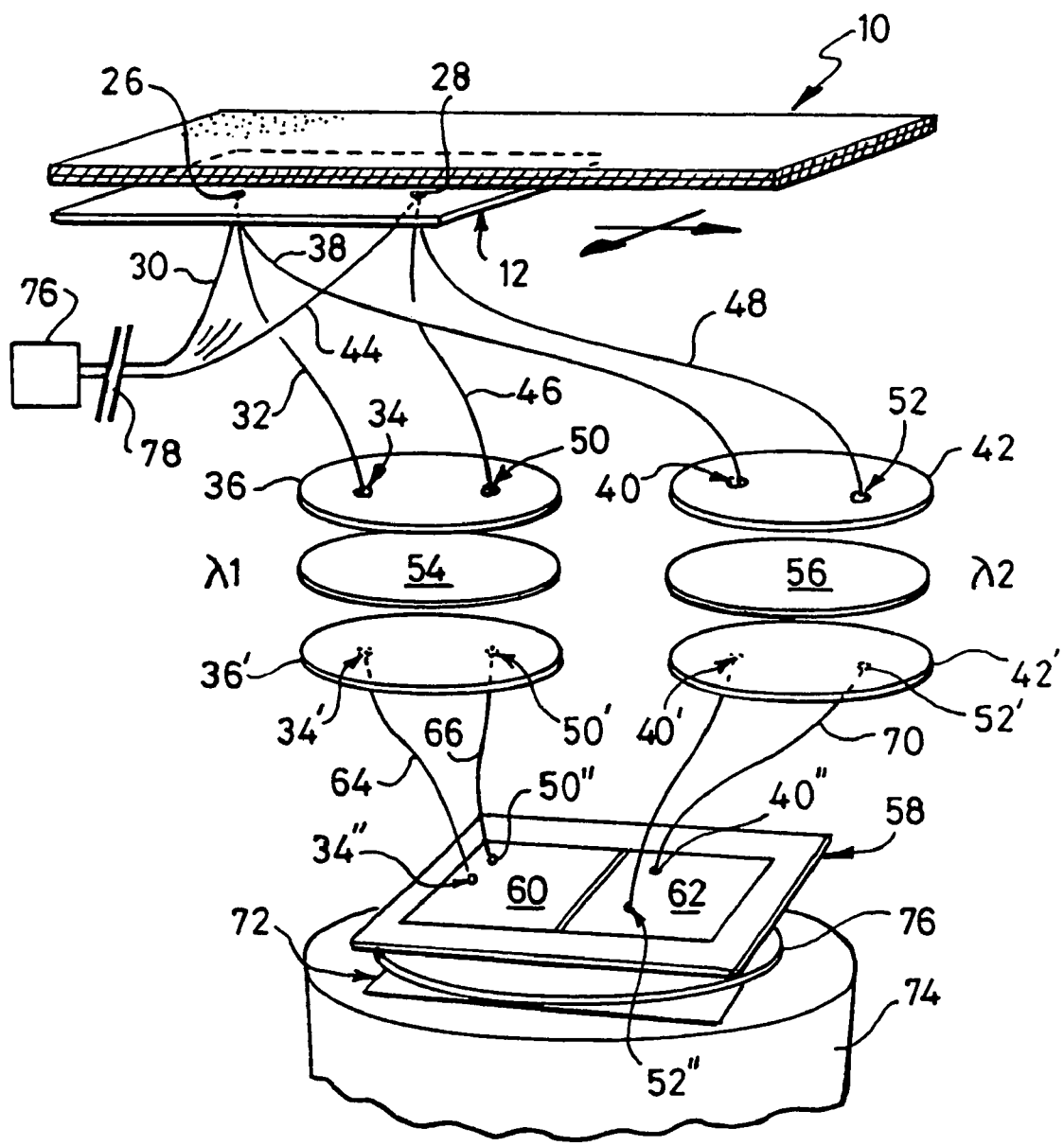
Figure 3:
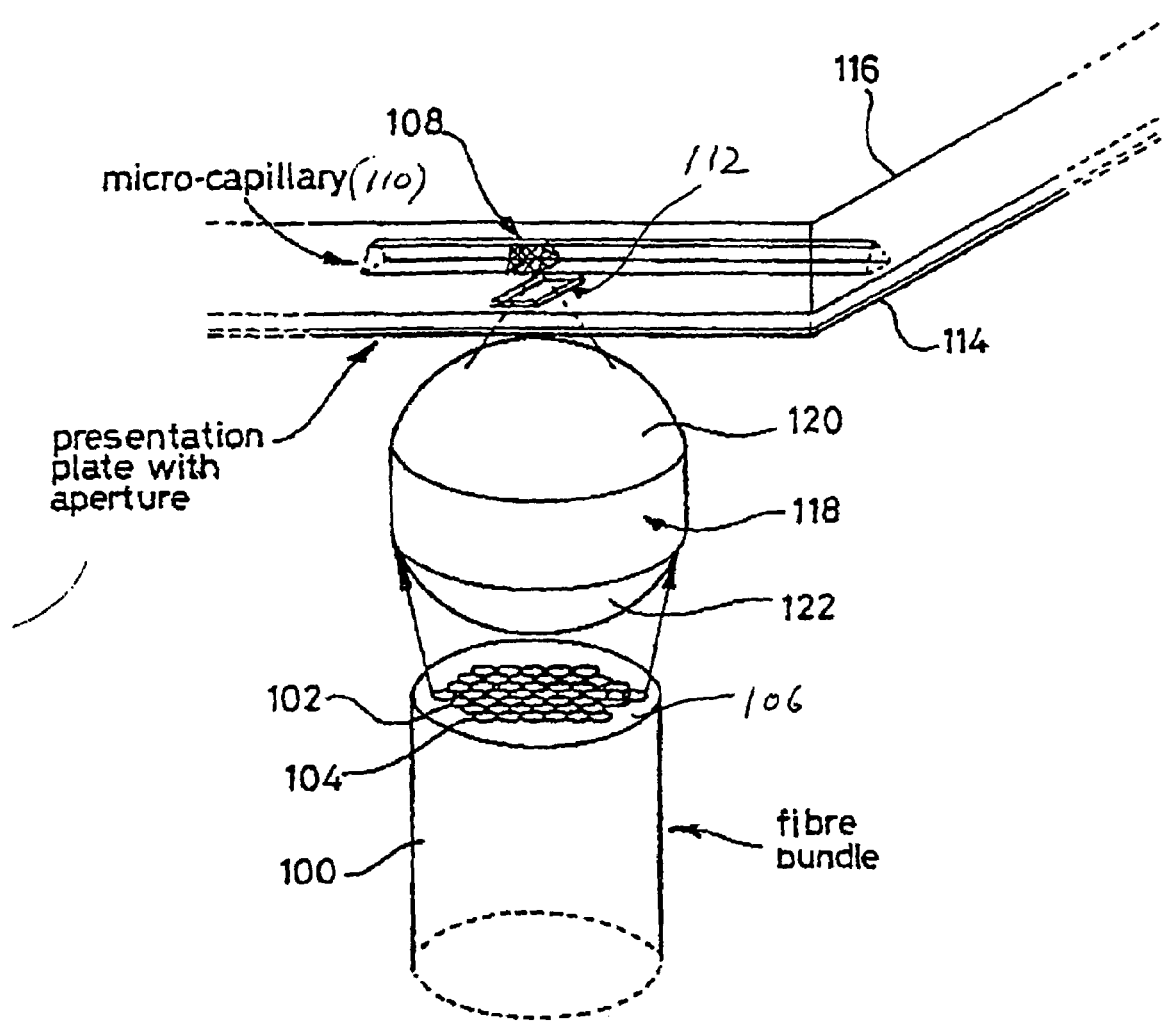

FIG. 2 of the accompanying drawings, which illustrates somewhat diagrammatically how a large number of separate fibre optic bundles can be arranged to inspect a corresponding number of sample sites in a multi-site array such as a multiwell plate for conveying light to selected regions of a charge coupled device, and FIG. 3 of the accompanying drawings, which illustrates the adaptation of a fibre bundle in accordance with the present invention whereby to allow micro-samples to be imaged by the same fibre bundles as envisaged in FIG. 2.

In FIG. 2, a well plate 10 is shown located above a presentation plate 12. The drawing is an exploded perspective view and the spacing implied by the drawing is an exaggeration of the actual spacing. In practice the presentation plate 12 will be very close to the underside of the well plate 10.

Well plates have tended to be constructed with either 96 wells typically arranged in 8 rows of 12 columns, but in recent years higher density plates have been constructed and a typical high density plate may contain, say, 36 times as many wells as the 96 well plate. However the area of the plate is the same as is the basic matrix. The only difference in this case is that the well size has been decreased enabling six wells to be located along each row and six wells down each column in place of a single well in the original array. This means that instead of there being twelve wells along each row, there are now 72 and instead of there being eight rows, there are now 48 rows.

To take advantage of this and to simplify the indexing of a 96 aperture presentation plate, the latter is formed with openings which correspond in position to each of the original 96 wells of a 96 well plate, but equal in size to that of the wells in the 3456 well plate. This means that 96 of the 3456 wells can be inspected simultaneously by aligning the presentation plate 12 so that the first of the 96 apertures coincides with the first of the 3456 wells in the well plate. This means that the second aperture in the presentation plate aligns with the seventh well along the first row, and so on.

Shifting the presentation plate 12 by a distance equal to the distance between successive wells in the first row means that all of the 96 apertures in the presentation plate 12 will now be aligned with a new set of 96 of the wells in the well plate 10. By moving the presentation plate successively through six steps parallel to the first row, and for each step six positions perpendicular to that row, in each case each movement corresponding to the distance between adjoining wells in the well plate measured perpendicular to the first row, so every one of the 3456 wells can be interrogated by 36 relative movements between the presentation plate and the well plate.

In practice, the well plate is moved relative to the presentation plate.

Each of the apertures in the presentation plate 12 serves as a termination for a fibre bundle made up of 45 individual fibres. The fibres are shown terminating in two of the apertures for illustration only, one designated 26 and the other 28.

Each bundle of 45 fibres is made up of three groups of 15, one group such as 30 extending to an excitation light source, one group such as 32 conveying fluorescence light from a well aligned with the aperture 26 to an aperture 34 in a presentation disc 36. The third group of 15 fibres 38 extends to another opening 40 in a second presentation disc 42, for confiding fluorescence light to that other opening 40.

The three groups of 15 fibres making up the other illustrated bundle leading to and from aperture 28 are denoted by reference numerals 44, 46 and 48 respectively and these extend from the excitation light source in the case of group 44 and to two other apertures 50 and 52 respectively in the two presentation discs-36 and 42.

Each of the latter includes 96 apertures arranged regularly over the circular area of each disc, and similar discs 36' and 42' are aligned with the discs 36 and 42. Suitable optical filter discs 54 and 56 are sandwiched between discs 36 and 36', and discs 42 and 42'.

Apertures in the two discs 36, 36' (42, 42) are aligned on a one to one basis and fibres lead from each of the aligned apertures such as 34' in disc 36' to unique apertures in two groups of 96 apertures arranged in a rectilinear matrix in an output plate generally designated 58. The first such matrix is designated 60 and the second 62 and the fibres such as 64 from aperture 34' and 50' lead to apertures 34" and 50" in the matrix region 60 and the fibres 68 and 70 from apertures 40' and 52' in disc 42' lead to apertures such as 40" and 52" in matrix 62.

The two matrixes 60 and 62 together form a generally square outline which conforms approximately to the square aspect ratio of an input window illustrated at 72 in a camera 74.

The excitation light source is denoted by reference numeral 76 and between it and the 96 groups of 15 fibres such as 30 and 44 is located a filter 78. 42 is as shown in FIG. 2. Two of the openings are arbitrarily shown at 34 and 36.

In summary it is important to observe that two examples of the large number of fibre optic bundles are illustrated at 26 and 28 in FIG. 2, and the fibres making up each of the bundles are split into three, some such as 30 and 44 going to a light source 76 for conveying excitation radiation from the light source 76 to the microwells or other sample sites in the plate 10 and the other two parts of each bundle, each containing a similar number of fibres, are conveyed to appropriate regions such as 34 and 40 in the case of 26 and 50 and 52 in the case of 28, of the output ends of the fibre bundles for the reasons mentioned previously.

It is also to be understood that the detector system illustrated in FIG. 1 is only intended to be illustrative of one type of muti-channel epi-fluorescent system to which the present invention can be applied and is not intended to be limiting on the scope of the invention as described herein.

Turning now to FIG. 3, this shows the upper end of a fibre bundle generally designated 100 containing typically 50 or 100 or more fibres, some of which are shown exposed in the input end of the bundle 100 at 102, 104. The central axis of the bundle which corresponds to the centre of the generally circular input end 106 is generally aligned with the centre of a small sample which in the example shown is designated by 108 and comprises a small segment of a capillary or microcapillary 110 which extends over a length of between one and a few mm in a multi sample plate.

In registry with the region of interest, is one aperture 112 in a multi-aperture plate generally designated 114 which has a regular array of apertures located therein corresponding to the positions along each of the capillaries 110, which are to be inspected for the purposes of performing the assay.

The test involves the simultaneous excitation of all of the areas such as 108 and the subsequent detection of fluorescence given off by any cells or cell clusters in the sample region during an interrogation which may extend for a very short period of time or a longer period of time on the nature of the test after the excitation radiation has ceased.

In addition the inspection interval may not occur instantaneously after the excitation radiation has been removed from the sample, but may begin a short interval of time after the end of the excitation phase.

To assist in relating FIG. 3 to FIG. 2, the sample 108 can be thought of as comprising the sample site closest to the nearest right hand corner of the plate 10 of FIG. 2, and the apertured plate 114 can be thought of as being similar to the apertured plate 12 except that as shown in FIG. 3, it has been moved relative to the sample plate 10 so as to align with the nearest right hand corner of the plate shown in FIG. 2. To this end the capillary 110 is contained within a presentation plate, typically formed from plastics material and conventionally referred to as a plastic fluid presentation chip.

By moving a plate 114 containing a small aperture such as 112 relative to the plate 116, so the aperture can register relative to different regions along the same capillary each of which can be thought of as a separate sample site, or a single region of each of a plurality of shorter capillaries is investigated as the plate is moved so that the aperture or window 112 aligns with the selected region of each of the capillaries.

In general it is important for the axis of the bundle 100 to align with the central region of the sample 108 which is typically of the order of 100×100 microns, but if the window aperture 112 is large enough, it may be possible to step the plate through two or three 100 micron steps to present different regions of the capillary to the bundle 106 without moving the latter since light will still be received by the ends of the fibres even when the optical axis of the bundle is misaligned with the central region of the area of interest defining the sample for the time being.

In general however it is assumed that the bundle will be moved so that the bundle axis will always be aligned with the central region of the sample.

In accordance with the invention, the light gathering properties of the fibre optic bundle end face 106 are significantly enhanced by using a drum lens 118 located between the window aperture 112 and the fibre optic end face. The distance between the convex surface 120 and the aperture 112 is arranged to be very small whilst that between the convex surface 122 at the other end of the drum lens and the fibre optic input face 106 is considerably greater. The distance is determined by the numerical aperture of the relevant input face and by selecting a micro drum lens having a very high numerical aperture (typically 0.7 as opposed to the lower numerical aperture of perhaps 0.2 associated with the fibre optic bundle end face 106), so a smaller distance between the convex surface 120 and the sample 108/window 112 can be used thereby increasing the amount of light emitted from the sample which will be collected by the input face 120 of the drum lens 118.

The drum lens is preferably formed from high quality sapphire.

One lens 118 and one bundle 100 are provided for each of the plurality of simultaneous inspection sites which are to make up the assay and by fixing the lenses and bundles relative one to the other in a matrix array, and moving the presentation plate 116 and the apertured plate 114 relative thereto, so different sample sites either micro wells or regions of micro- capilliaries such as shown, can be presented to the large number of lenses and fibre bundles simultaneously.

As previously mentioned, all of the sites or wells in a high density array can be inspected by stepping the high density array relative to the matrix and lenses and fibre bundles so that if for example there are 96 in the array, and there are four times that number of sites to be inspected, a 2×2 stepping of the presentation plate relative to the matrix array will allow all of the 384 sites to be inspected in four groups of 96.

Although described in relation to the multi-channel arrangement of FIG. 2, the arrangement shown in FIG. 3 can in its simplest form comprise a single channel assay inspection device in which a single fibre optic bundle 100 and drum lens 118 is positioned below a plate having a plurality of sample sites thereon and the plate is indexed relative to the optics 100/118 or vice versa to enable light from each sample site in turn to be projected into the input surface 120 of the lens 118.

Although shown in relation to the underside of a sample array, it is to be understood that the optical elements 100 and 118 and the apertured plate 114 may be inverted relative to the presentation plate 116 and each of the sample sites inspected from above instead of from below.

In this event, the trapezoidal section of each capillary is preferably inverted relative to that shown in FIG. 3 so that the wider base is presented to the window above the plate. Where parallel sided wells are concerned, it is of less importance whether they are viewed from above or below provided that if the cells or cell clusters which are emitting fluorescence light are located near the base of the well, the attenuation of the fluorescence up through the liquid medium within the well is not too great to prevent suitable detection from above.

What is claimed is:

1. A system for imaging radiation emitted by assay samples onto a photoelectronic detector, wherein an additional optical imaging device is located at the input end of a fibre optic bundle of an imaging system said bundle being adapted to convey light from the input end thereof to a photosensitive detector, the properties of the additional device being such as substantially to match the size of the input end of the bundle to the size and NA of a micro-sample by appropriate choices of numerical aperture for the additional device, so as to reduce the field of view of the bundle to substantially the area of the region of interest of a micro-sample to allow the bundle to view just one micro-sample, and secondly to increase the light collecting properties of the bundle in relation to small light emitting areas.

2. A system according to claim 1, in which said photosensitive detector comprises a CCD array.

3. A system according to claim 1, wherein, where the bundle has a diameter of typically 14 nm and an NA typically of 0.22, the optical device requires to have a NA of approximately 0.7 if the sample has a diameter of the order of 130 microns.

4. A system according to claim 3, wherein the combination of the additional optical device with a background reducing aperture, is effective to increase the light collecting properties of the bundle per unit volume of the sample, by a factor in the range 10 to 20.

5. A system according to claim 1, wherein the additional optical device comprises a microlens.

6. A system according to claim 5, wherein the optical device is a ball lens.

7. A system according to claim 5, wherein the additional device is a drum lens.

8. A system according to claim 5, wherein each microlens has an anti-reflective coating selected to take account of the range of excitation and emission wavelengths associated with the assay.

9. A system according to claim 5, wherein each microlens is constructed from low fluorescence material having a selected refractive index.

10. A system according to claim 5 wherein the microlens material comprises high quality sapphire.

11. A system according to claim 1 wherein an apertured plate is located between the samples and the input end of the bundle, each aperture being aligned with one of the micro-samples, and the additional device is located between the aperture and the bundle which is to receive light from that aperture.

12. A system according to claim 11, wherein, when the samples are generally circular, the apertures are also general circular.

13. A system according to claim 11, wherein, when the samples are elongate, the aperture may be square or rectangular and dimensioned to allow for tolerance in the size and lateral position of the micro-samples as determined by the lateral position of a sample in a sample array.

14. A system according to claim 13, wherein the samples are microcapillaries.

15. A system according to claim 11, wherein the sample is systematically scanned.

16. A system according to claim 15, wherein the sample is scanned by moving the plate containing microcapillaries or microwells relative to an array of fibre optic bundles and associated microlenses.

* * * * *